US006187052B1

United States Patent
Molino et al.

(10) Patent No.: US 6,187,052 B1
(45) Date of Patent: Feb. 13, 2001

(54) PROSTHETIC ANKLE JOINT

(76) Inventors: Joseph L. Molino, 2 Aura Dr., Valley Cottage, NY (US) 10989; Michael Rebarber, 28 Buckingham Pl., Glen Rock, NJ (US) 07452

( * ) Notice: Under 35 U.S.C. 154(b), the term of this patent shall be extended for 0 days.

(21) Appl. No.: 09/353,502

(22) Filed: Jul. 14, 1999

(51) Int. Cl.⁷ .................................................. A61F 2/66
(52) U.S. Cl. .................................. 623/52; 623/47
(58) Field of Search .................... 623/39, 40, 41, 623/42, 43, 47, 48, 49, 50, 51, 52, 53, 54, 55

(56) References Cited

U.S. PATENT DOCUMENTS

| | | | |
|---|---|---|---|
| 2,208,275 | * 7/1940 | McCann | 623/40 |
| 3,779,654 | * 12/1973 | Horne | 403/62 |
| 3,871,032 | * 3/1975 | Karas | 3/1.2 |
| 4,446,580 | * 5/1984 | Furuya et al. | 3/6 |
| 5,030,239 | 7/1991 | Copes . | |
| 5,158,570 | 10/1992 | Schey et al. . | |
| 5,181,931 | * 1/1993 | Van De Veen | 623/40 |
| 5,405,411 | 4/1995 | McCoy . | |
| 5,425,780 | 6/1995 | Flatt et al. . | |
| 5,443,527 | 8/1995 | Wilson . | |
| 5,545,234 | 8/1996 | Collier, Jr. . | |
| 5,571,210 | * 11/1996 | Lindh | 623/38 |
| 5,571,212 | * 11/1996 | Cornelius | 623/48 |
| 5,766,264 | 6/1998 | Lundt . | |
| 5,769,896 | 6/1998 | Rosendahl et al. . | |
| 5,800,562 | 9/1998 | Wilkinson . | |
| 5,800,566 | * 9/1998 | Gramnas | 623/39 |
| 5,800,567 | * 9/1998 | Cooper et al. | 623/39 |
| 5,800,568 | 9/1998 | Atkinson et al. . | |
| 6,077,301 | * 6/2000 | Pusch | 623/53 |

* cited by examiner

Primary Examiner—Michael J. Milano
Assistant Examiner—Alvin Stewart
(74) Attorney, Agent, or Firm—Lawrence G. Fridman

(57) ABSTRACT

An articulated prosthetic ankle joint is adapted for connection between a pylon and a prosthetic foot for moving the foot between dorsiflexed and plantarflexed positions during human locomotion. The prosthetic ankle joint includes a base member adapted for connection to the prosthetic foot, a bracket member adapted for connection to the pylon and pivotally connected to the base member, a recumbent bar pivotally connected to the bracket member, and an upright bar having a lower end pivotally connected to the base and an upper end pivotally connected to the recumbent bar. The bracket member together with the base member, the recumbent bar and the upright bar form a four-bar linkage assembly with a deformable interior space. An elastomeric block is captured within the interior space. Pivotal movement of the base member with respect to the bracket member between dorsiflexed and plantarflexed positions causes deformation of the interior space, and thus deformation of the resilient block. The resilient block normally biases the base member to the dorsiflexed position and resists rotational movement of the base member from the dorsiflexed position.

19 Claims, 11 Drawing Sheets

FIG. 7

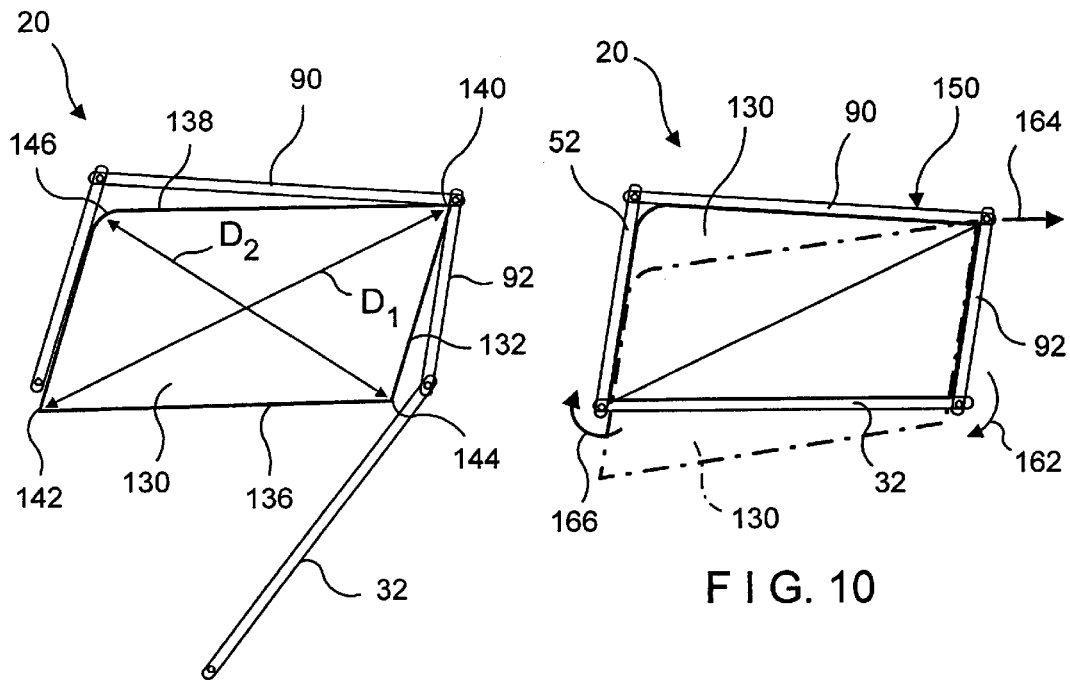
FIG. 9
FIG. 10
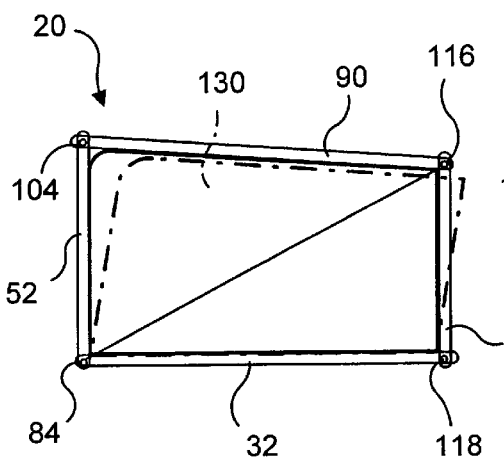
FIG. 11
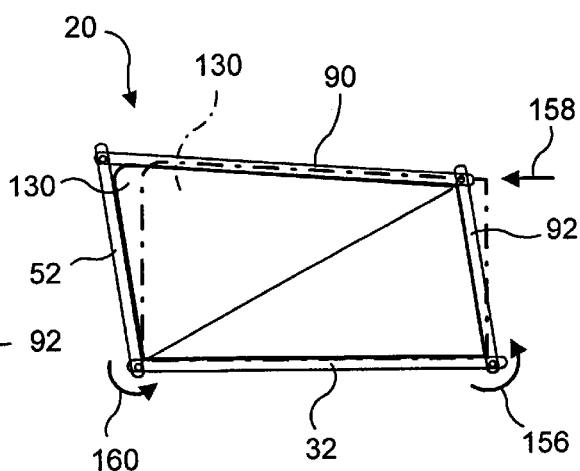
FIG. 12

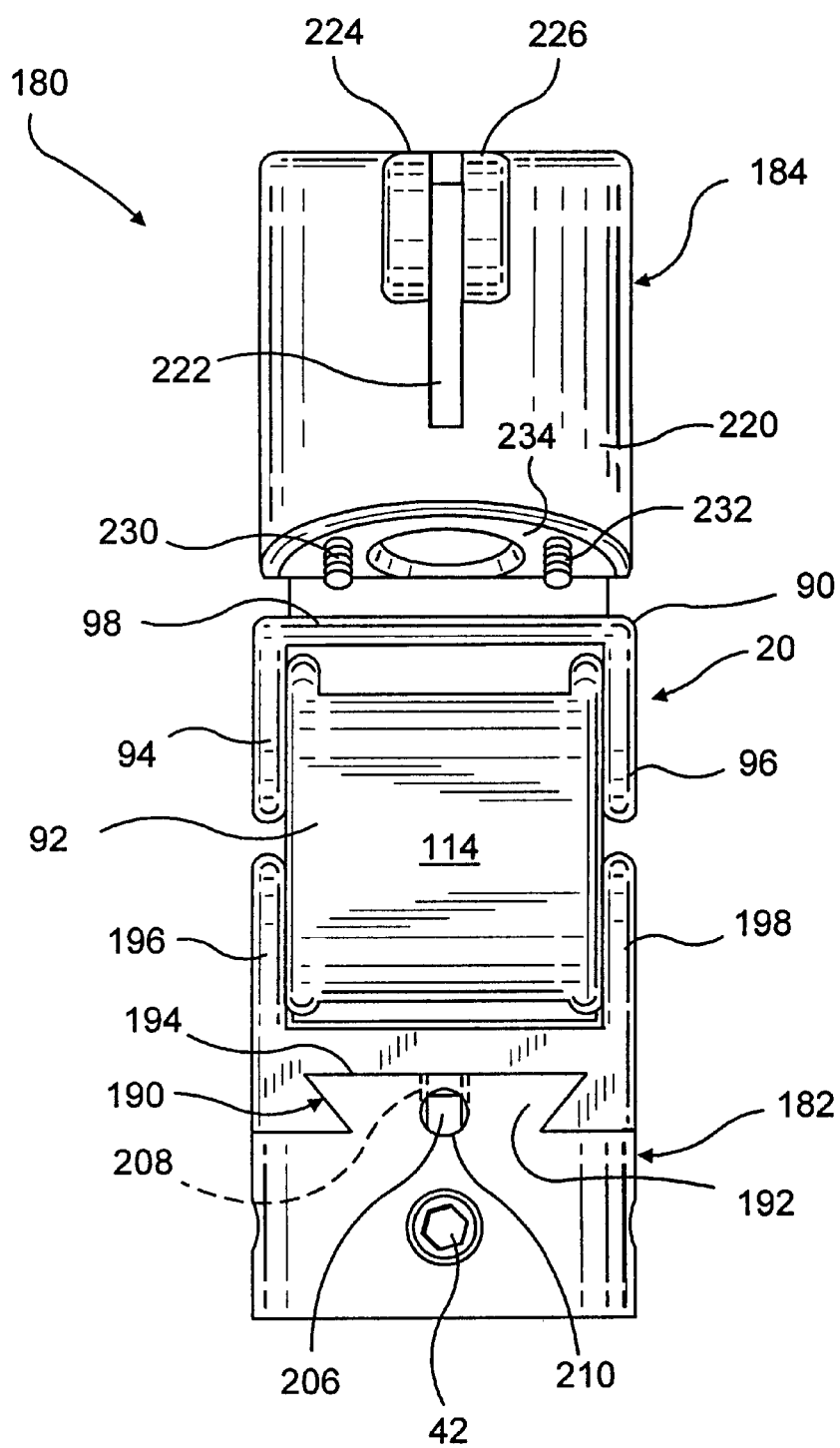
F I G. 14

PROSTHETIC ANKLE JOINT

BACKGROUND OF THE INVENTION

1. Field of the Invention

This invention relates in general to prosthetic devices, and more particularly to articulated prosthetic ankle joints.

2. Description of the Related Art

Currently available prosthetic ankle joints are heavy, bulky, and do not provide a range of motion that imitates a normal foot range of motion during walking. Each foot and ankle during walking travel through stance and swing phases of a gate cycle. In the stance phase, the foot is in contact with the ground and the weight of a person is supported on the foot. In the swing phase, the foot is off the ground as the entire leg and foot move from a posterior position to an anterior position with respect to a center of gravity of the person. The stance phase begins just after completion of the swing phase and commences with a heel strike wherein the foot is lowered to the ground as the body moves forward from a position posterior to the person's center of gravity. Immediately after heel strike, the foot moves from a dorsiflexed position, wherein the toes of the foot are pointed upwards, to a plantarflexed position wherein the bottom of the foot or shoe is flat on the walking surface, which provides greater stability as the entire weight of the person is shifted over the foot in contact with the ground. The swing phase commences just after heel strike of the other foot. During the swing phase, the foot is again in the dorsiflexed position as the foot leaves the walking surface and the foot and leg swing forward in preparation for the stance phase. Dorsiflexion is very important for normal human locomotion, since the toes must be dorsiflexed in order to clear the floor. If the foot were not dorsiflexed during the swing phase, it would most likely catch on the walking surface and cause the person to stumble and fall, leading to potentially serious injury.

With an amputee, it is customary to make the prosthetic limb about ⅜ to ½ inch shorter than the natural limb in order to provide adequate ground clearance for the prosthetic limb during the swing phase. Consequently, the amputee develops an unnatural gate pattern, causing him or her to lean to one side while walking. Over the years, this unnatural gate pattern may cause hip, pelvis, knee and back problems.

In addition, most prosthetic feet and ankle systems are fixed at 90°. During heel strike of the prosthetic foot, the momentum of the person causes the foot to rotate forward to a more stable flat position on the walking surface. However, since there is no flexibility in the ankle, the person is lurched forward. As the person's center of gravity passes over the centerline of the foot, the knee is forced to bend to compensate for the unnatural movement. With above-knee amputees, the prosthetic knee joint may become unstable and cause unwanted or unexpected knee flexure, and may cause the person to fall.

SUMMARY OF THE INVENTION

The present invention overcomes many of the drawbacks of the prior art by the provision of a prosthetic ankle joint that mimics natural ankle motion during walking.

According to the invention, a prosthetic ankle joint is adapted for connection between a pylon (or other interface between the prosthetic ankle joint and the stub of an amputee) and a prosthetic foot for moving the foot between dorsiflexed and plantarflexed positions. The prosthetic ankle joint comprises a base member adapted for connection to the prosthetic foot, a bracket member adapted for connection to the pylon or other interface, and a collapsible and expandable linkage assembly. The linkage assembly includes a first recumbent bar at least operatively associated with the base member, a first upright bar having a lower end pivotally connected to the first recumbent bar at a first pivot joint and an upper end fixedly connected to the bracket member, a second upright bar having a lower end pivotally connected to the first recumbent bar at a second pivot joint, and a second recumbent bar pivotally connected between the first and second upright bars at third and fourth pivot joints, respectively. The first and second upright bars together with the first and second recumbent bars form an interior space. With this arrangement, pivotal movement between the bracket member and the base member between dorsiflexed and plantarflexed positions causes deformation of the interior space.

Preferably, a resilient member, such as a spring, piston, resilient block, or the like, is positioned in the interior space and is deformable upon deformation of the interior space. The resilient member normally biases the base member in the dorsiflexed position and resists rotational movement of the base member from the dorsiflexed position.

Further according to the invention, a prosthetic ankle joint is adapted for connection between a pylon (or other interface) and a prosthetic foot for moving the foot between dorsiflexed and plantarflexed positions. The prosthetic ankle joint comprises a base member adapted for connection to the posthetic foot, a bracket member adapted for connection to the pylon or other interface and pivotally connected to the base member at a first pivot joint, a recumbent bar pivotally connected to the bracket member at a second pivot joint, and an upright bar having a lower end pivotally connected to the base member at a third pivot joint and an upper end pivotally connected to the recumbent bar at a fourth pivot joint. The bracket member together with the base member, the recumbent bar and the upright bar form an interior space. With this arrangement, pivotal movement between the bracket member and the base member between dorsiflexed and plantarflexed positions causes deformation of the interior space.

Preferably, a resilient member is located in, and at least substantially fills the inner space to bias the base member to the plantarflexed position and resist rotational movement of the base member from the plantarflexed position.

Other objects and advantages of the invention will become apparent upon reading the following detailed description and appended claims, and upon reference to the accompanying drawings.

BRIEF DESCRIPTION OF THE DRAWINGS

The preferred embodiments of the present invention will hereinafter be described in conjunction with the accompanying drawings, where like designations denote like elements throughout the drawings, and:

FIG. 7 is a side elevational view of the prosthetic ankle joint in a plantarflexed position;

FIG. 9 is a diagrammatic view of a four-bar linkage assembly that forms part of the prosthetic ankle joint according to the present invention;

FIG. 10 is a diagrammatic view of the four-bar linkage assembly in a dorsiflexed position;

FIG. 11 is a diagrammatic view of the four-bar linkage assembly in a mid-stance position;

FIG. 12 is a diagrammatic view of the four-bar linkage assembly in a plantarflexed position;

FIG. 14 is a front plan view of the prosthetic ankle joint of FIG. 13.

DETAILED DESCRIPTION OF THE PREFERRED EMBODIMENT

Figure 1:
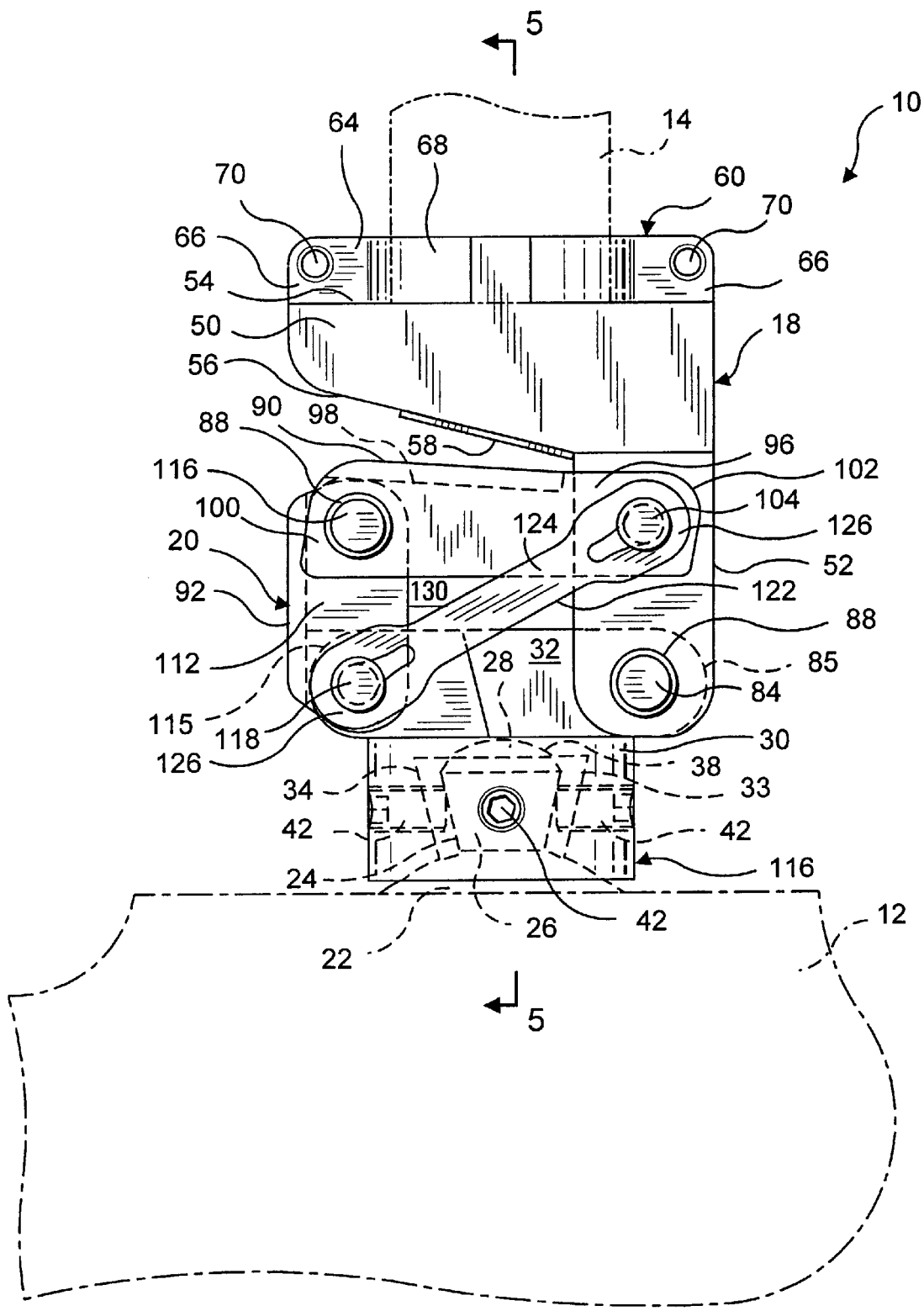
FIG. 1 is a side elevational view of a prosthetic ankle joint according to the invention.
Figure 2:
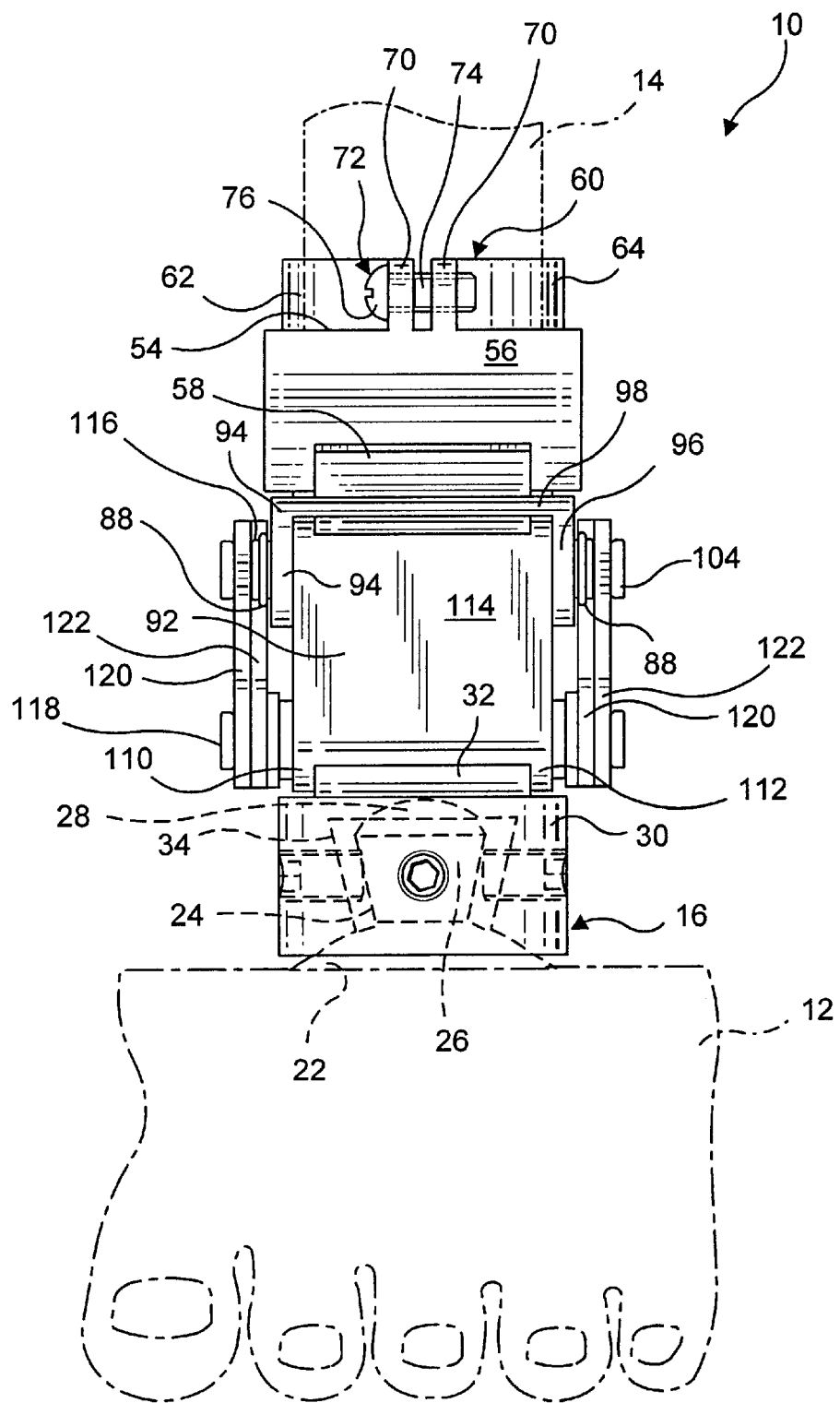
FIG. 2 is a front elevational view of the prosthetic ankle joint according to the invention.
Figure 3:
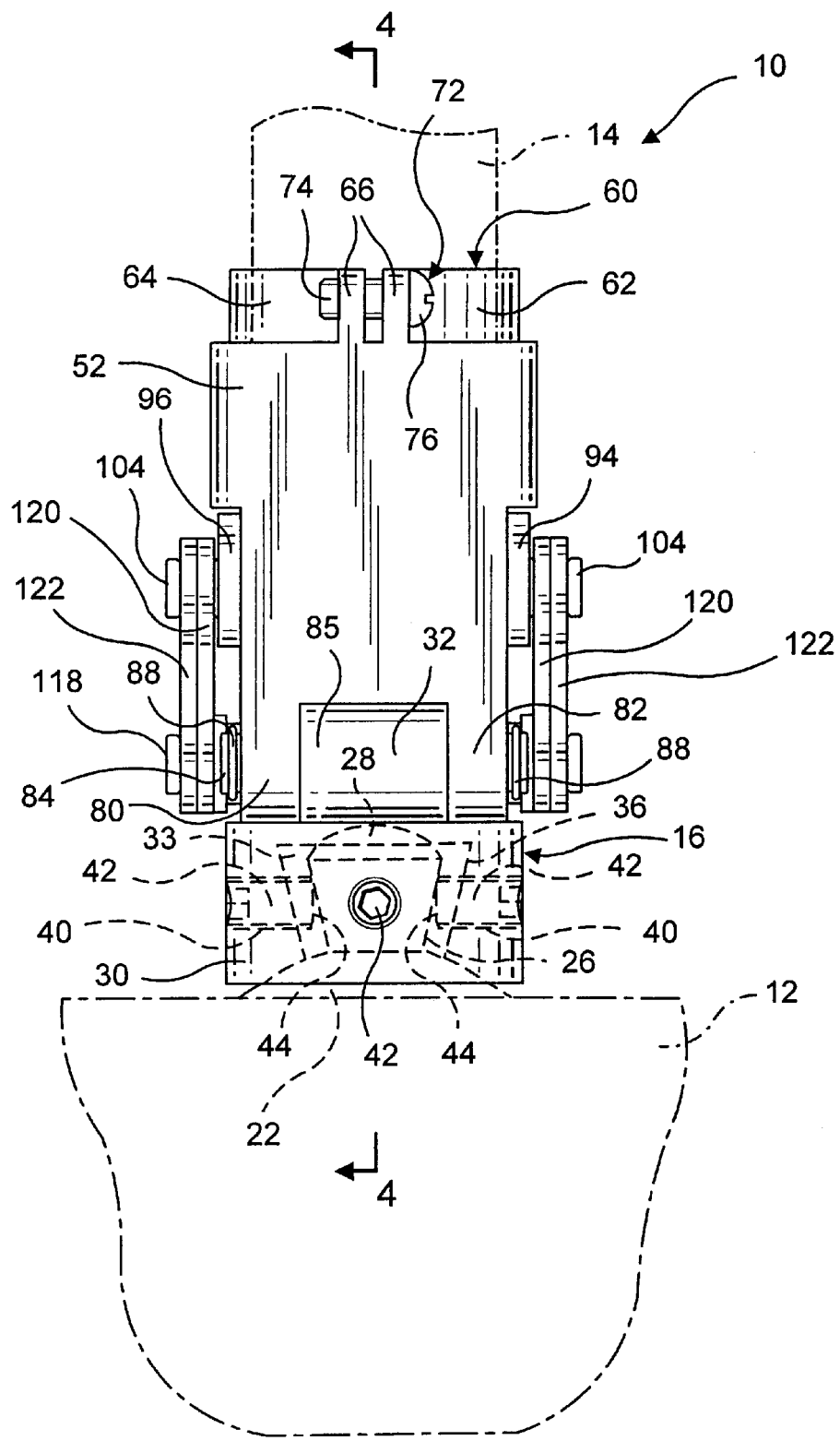
FIG. 3 is a rear elevational view of the prosthetic ankle joint according to the invention.

Referring now to the drawings, and to FIGS. 1 to 3 in particular, a prosthetic ankle joint 10 according to the invention is adapted for connection between a prosthetic foot 12 (shown in phantom line) and a prosthetic lower leg section or pylon 14 (also shown in phantom line). The prosthetic ankle joint 10 includes a base assembly 16, a torque bracket 18 pivotally connected to the base assembly 16, and a four-bar linkage assembly 20 pivotally connected to the base assembly 16 and the torque bracket 18.

A semi-spherical connection element 22 fits within a depression (not shown) of the foot 12. A central boss 24 (shown in hidden line) is preferably of inverse frustroconical configuration and projects upwardly from the semi-spherical element 22. The formed inverse frustrocone has a substantially uniform surface 26. An upper end 28 of the central boss 24 is semi-spherical in shape to permit adjustment of the base assembly 16 with respect to the foot 12. In an alternative arrangement, the surface 26 of the central boss 24 may be multi-faceted.

Figure 4:
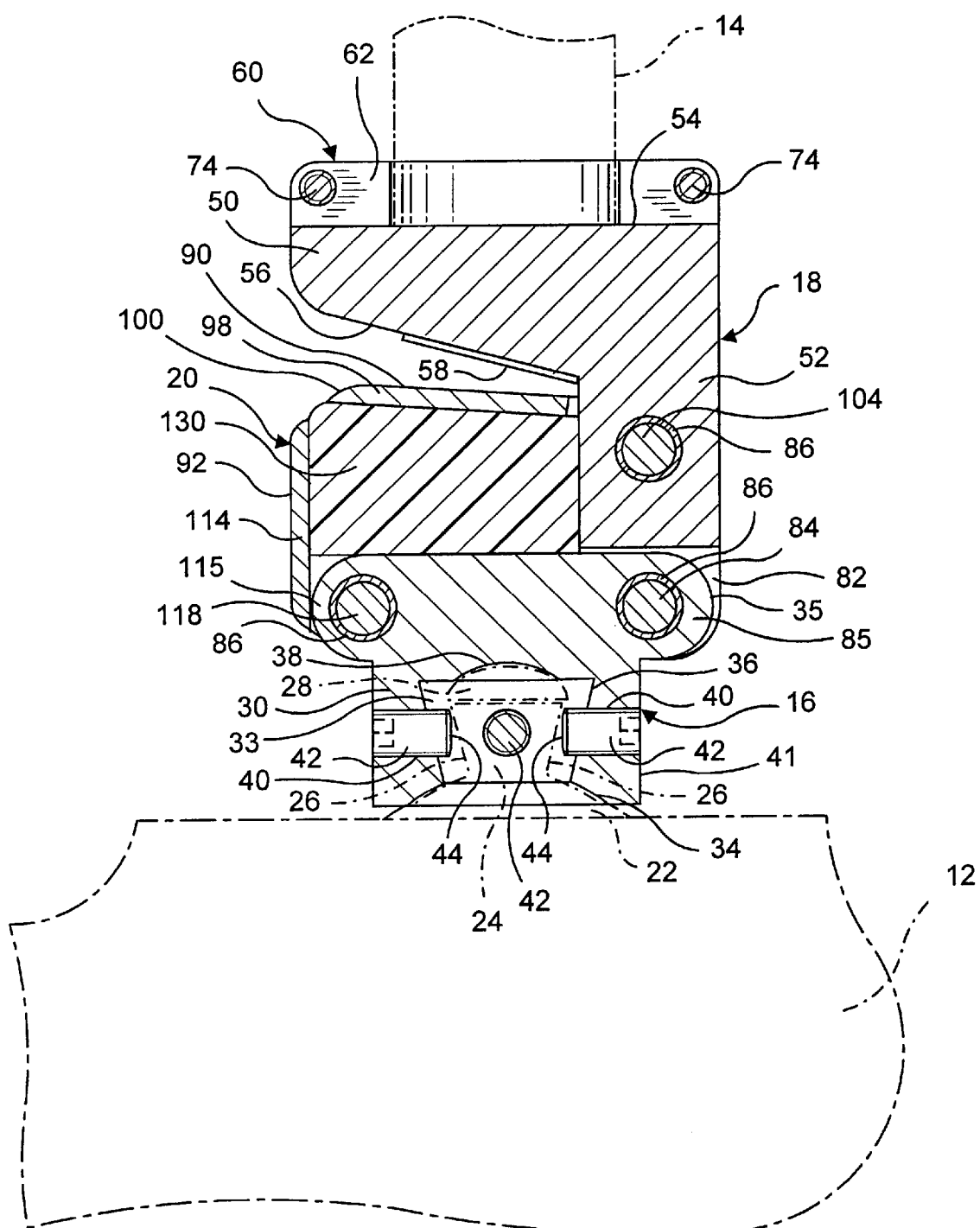
FIG. 4 is a cross sectional view of the prosthetic ankle joint taken along line 4—4 of FIG. 3.

As shown most clearly in FIGS. 3 and 4, the base assembly 16 contains a lower base portion 30 and an upper base portion 32 which can be formed as a unitary member or two individual portions. The lower base portion 30 is substantially cylindrical in configuration and includes an opening 33 with a first inner surface 34 that is complementary in shape to the semi-spherical connection element 22, and a second inner surface 36 that is adapted to receive the surface 26 of the central boss 24. Likewise, the upper base portion 32 includes a semi-spherically shaped inner surface 38 that is complementary in shape to the upper end 28 of the boss 24. The inner surfaces 34, 36 and 38 are spaced from their respective complementary elements 22, 26, and 28 so as to provide adjustment between the foot 12 and the base assembly 16. Apertures 40 are formed at equally spaced intervals around the circumference of the lower base portion 30. The apertures 40 extend radially inwardly from an outer surface 41 of the lower base portion 30 to the second inner surface 36 thereof. Preferably, four apertures 40 are formed at 90° intervals around the circumference of the lower base portion 30. Each aperture is preferably threaded and receives a set screw 42. Each set screw 42 includes an inner end 44 that abuts the surface 26 of the boss 24. The position of the foot 12 with respect to the lower base portion 30 can be adjusted by varying the distance that the studs project into the opening 33 of the lower base portion. In this manner, both lateral and longitudinal adjustments are made possible to accommodate users of different weight, height, shoe size, stride length, and so on. When the boss 24 is multi-faceted, the faces (not shown) are aligned with the inner end 44 of one of the set screws 42. This arrangement also provides rotational adjustment of between the foot and the prosthetic ankle joint.

With additional reference to FIGS. 1 and 2, the bracket 18 is generally inverse L-shaped in configuration and includes an upper arm 50 that extends in a generally horizontal direction and a lower depending arm 52 that extends downwardly from the upper arm 50. The upper arm 50 includes an upper surface 54 and a lower surface 56 that extends downwardly at an acute angle with respect to the upper surface toward the depending arm 52. A resilient pad 58 is mounted on the lower surface 56 for a purpose to be described in greater detail hereinbelow.

A mounting bracket 60 extends upwardly from the upper surface 54 of the upper arm 50 and includes a receiving arrangement with a pair of opposed mounting bracket elements 62, 64. Each mounting bracket element 62, 64 has a pair of flat sections 66 separated by a curved section 68. The curved sections 68 of the receiving arrangement face each other to form a split cylindrical sleeve adapted to receive the pylon 14. The receiving arrangement contains a securing element having aligned openings 70 (See FIG. 1) formed in each flat section 66 of the mounting bracket elements 62, 64. Preferably, the openings 70 on the bracket half 64 are threaded. A fastener 72 (FIG. 2) is received in each of the aligned openings 70 of the bracket halves 62, 64. The fastener 72 has a head 76 that rests against the flat section 66 of the bracket half 62 and a threaded shaft 74 that extends through the opening 60 of the bracket half 62 and is threadably received in the opening 60 of the bracket half 64. With this arrangement, the pylon 14 can be secured to the prosthetic ankle joint 10 by inserting the pylon into the split cylindrical sleeve formed by the curved sections 68 and then rotating the fasteners to draw the bracket halves tightly against the pylon.

Although specific embodiments of the receiving arrangement and the securing element have been discussed hereinabove, it should be understood that any conventional means of connection between the pylon and the upper arm, as well as any conventional means of securing the pylon within the mounting bracket and the receiving arrangement are within the scope of the invention.

As shown most clearly in FIG. 3, a lower end of the depending arm 52 is bifurcated into a pair of lower arm portions 80, 82 that straddle a posterior end 85 of the upper base portion 32. A lower posterior shaft 84 extends through each of the lower arm portions 80, 82 and the upper base portion 32 and pivotally connects the torque bracket 18 to the base assembly 16. Preferably, a cylindrical bearing sleeve 86 (FIG. 4) constructed of brass, nylon, or the like, is mounted in the lower arm portions and the upper base portion, with the shaft 84 extending through the sleeve to thereby reduce friction and wear during movement between the torque bracket 18 and base assembly 16. A retaining ring 88 (See FIG. 3) is installed in annular grooves (not shown) formed at opposite ends of the shaft 84 to thereby prevent separation of the shaft from the torque bracket 18 and base assembly 16.

With reference again to FIGS. 1 and 2, the four-bar linkage assembly 20 comprises the upper base portion 32 which forms a lower recumbent bar, the depending arm 52 of the torque bracket 18 which forms a posterior upright bar, an upper recumbent bar 90 pivotally connected to the depending arm 52, and an anterior upright bar 92 pivotally connected between the upper bar 90 and the upper base portion 32.

The upper bar 90 is generally U-shaped in configuration and includes a pair of legs 94, 96 that are oriented generally vertically and a web 98 extending and interconnecting between the legs. The web 98 extends from an anterior end portion 100 of each leg 94, 96 and terminates short of a posterior end portion 102 of each leg. The posterior end portions 102 of the legs 94, 96 straddle the depending leg 52 of the torque bracket 18 (See FIG. 3, for example). An upper posterior shaft 104 extends through each of the posterior end portions 102 and the depending leg 52 and pivotally connects the upper recumbent bar 90 to the torque bracket 18. As with the lower posterior shaft 84, a cylindrical bearing sleeve 86 (FIG. 4) can be mounted in the posterior end portions 102 and the depending leg 52 with the shaft 104 extending therethrough.

Figure 5:
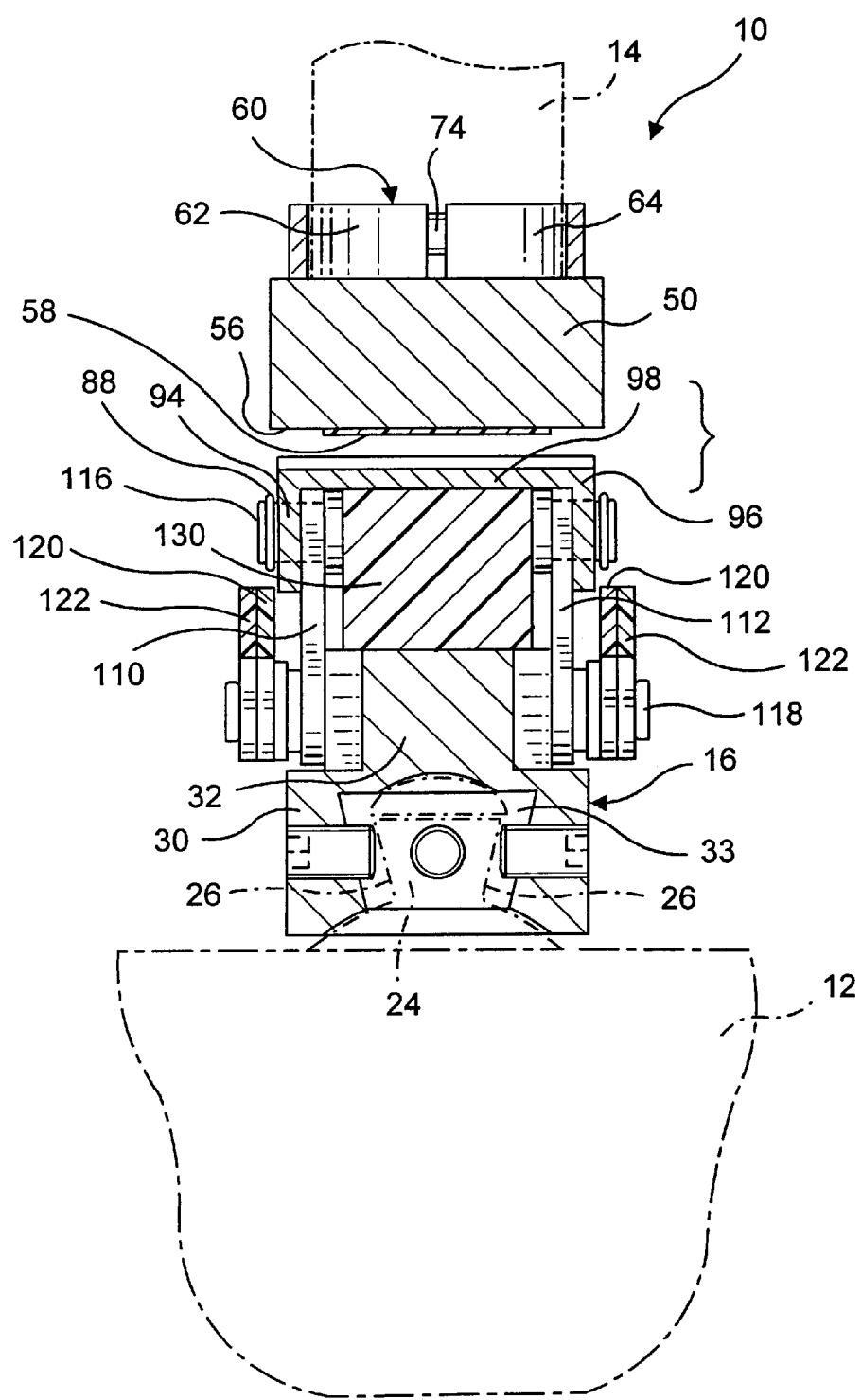
FIG. 5 is a cross sectional view of the prosthetic ankle joint taken along line 5—5 of FIG. 1.

With additional reference to FIGS. 2, 3 and 5, the anterior upright bar 92 is also generally U-shaped in configuration and includes a pair of legs 110, 112 that extend generally vertically and a web 114 that extends between the legs. As shown in FIGS. 1 and 2, for example, the web 114 has also a lower end portion of the legs 110, 112 which straddle an anterior end 115 of the upper base portion 32, while the anterior end 100 of the legs 94, 96 of the upper bar 90 straddle an upper end portion of the legs 110, 112. An upper anterior shaft 116 extends through each of the legs 110, 94, 112, and 96 and pivotally connects the upper recumbent bar 90 to the anterior upright bar 92. A retaining ring 88 is installed in annular grooves (not shown) formed at opposite ends of the shaft 116 to thereby prevent separation of the shaft from the upper recumbent bar 90 and the anterior upright bar 92. A pair of cylindrical bearing sleeves (not shown) can be mounted in legs 110, 94 and 112, 96 before installation of the shaft 116. A lower anterior shaft 118 extends through each of the legs 110, 112 and the upper base portion 32 and pivotally connects the anterior upright bar 92 to the base assembly 16. Preferably, a cylindrical bearing sleeve 86 (FIG. 4) is mounted in the legs 110, 112 and the upper base portion 32 with the shaft 118 extending through the bearing sleeve.

The upper posterior shaft 104 and lower anterior shaft 118 are preferably similar in construction and are longer than the lower posterior shaft 84 and the upper anterior shaft 116. A pair of inner and outer elongate biasing members 120 and 122 are connected to, and extend between common ends of the shafts 104 and 118 at least on one side, and preferably on both sides of the four-bar linkage 20. Each biasing member 120, 122 includes a straight section 124 terminated at opposite ends with a loop section 126. A groove (not shown) is formed at each end of the upper posterior shaft 104 and the lower anterior shaft 118 for receiving and holding the loop sections 126 of the biasing members 120, 122. As will be described in further detail below, the biasing members serve to hold or pull the prosthetic ankle joint 10 into a dorsiflexed position. The biasing members are preferably constructed of an elastomeric material. Depending on the height, weight, stride length and speed, shoe size, and other factors of a user, the stretchability or resistance to elongation of each of the biasing members may be adjusted by increasing or decreasing the length and/or durometer of the elastomeric material. In this embodiment, the biasing members also serve to prevent separation of the shafts 104 and 118 from the four-bar linkage. Although a total of four biasing members are shown, it is to be understood that more or less biasing members can be used. For example, the prosthetic ankle joint of the invention can be formed with the biasing members in the form of a pair of springs extending between the ends of the shafts 104 and 118. In some instances, the biasing members may be completely eliminated.

With reference to FIGS. 4 and 5, a resilient block 130 is captured within an inner space defined by the four-bar linkage assembly 20 and is in contact with the depending leg 52, the anterior upright bar 92, the upper recumbent bar 90, and the upper base portion 32. The resilient block is preferably constructed of an elastomeric material, such as rubber or polyurethane. Again, depending on the height, weight, stride length and speed, shoe size, and other factors of a user, the resiliency or resistance to deformation of the block 130 may be adjusted by increasing or decreasing the durometer of the elastomeric material.

With additional reference to FIGS. 9 and 10, the resilient block 130 is preferably of a parallelepiped configuration with an anterior side 132 extending substantially parallel to a posterior side 134, and a lower side 136 extending substantially parallel to an upper side 138. Before installation of the block 130 into the four-bar linkage assembly, the sides 132 and 138, as well as the sides 134 and 136, are initially oriented at an acute angle with respect to each other. In this manner, a diagonal distance D1 between an upper anterior corner 140 and a lower posterior corner 142 is longer than a diagonal distance D2 between a lower anterior corner 144 and an upper posterior corner 146 of the resilient block. During assembly, three of the bars of the four-bar linkage assembly 20 are pivotally connected together with their respective shafts while the fourth bar has only one end pivotally connected to the linkage assembly 20. As shown, the upper recumbent bar 90 is pivotally connected to the anterior upright bar 92 and the posterior upright bar or depending leg 52, while the lower recumbent bar or upper base portion 32 is pivotally connected at one end to the anterior upright bar 92. The resilient block 130 is then inserted into the interior of the four-bar linkage assembly 20 and the lower recumbent bar 32 is then rotated into place and pivotally connected to the posterior upright bar 52, as shown in FIG. 10. Although a specific way of installation of the four-bar linkage assembly has been described hereinabove, it should be understood that any alternative method of installation and positioning of the resilient block within the linkage assembly is within the scope of the invention.

Once installed, the shape of the resilient block 130 biases the four-bar linkage 20, and ultimately the prosthetic ankle joint 10, into a retracted or dorsiflexed position. Although a parallelepiped configuration is preferred for the resilient block 130, it is to be understood that the resilient block may be formed into other shapes, such as spherical, semispherical, pyramidal, and so on.

Figure 6:
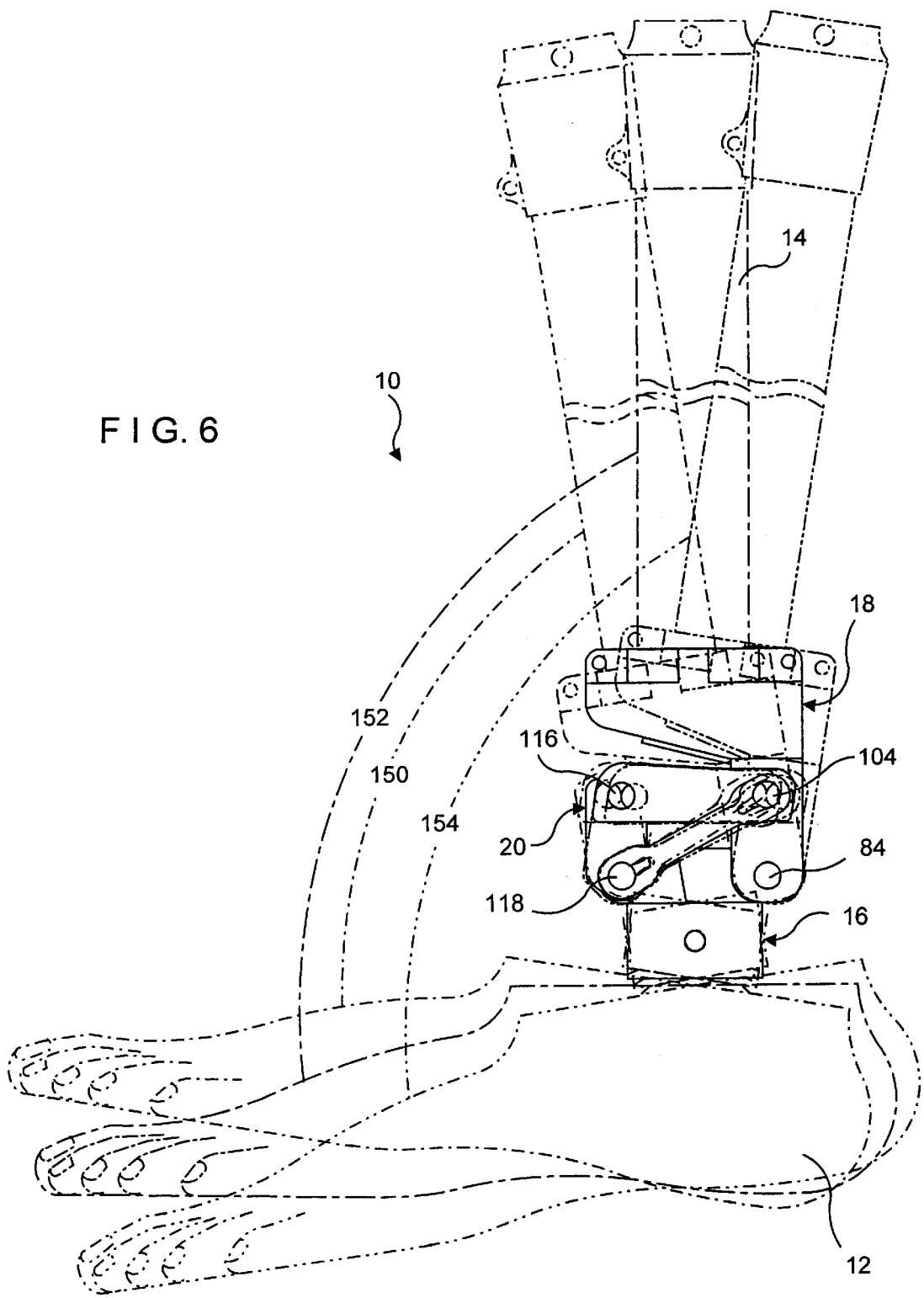
FIG. 6 is a side elevational view of the prosthetic ankle joint and illustrating the range of motion between plantar and dorsiflexed positions.

Turning now to FIGS. 6 to 8 and 10 to 12, the above-described arrangement permits movement of the prosthetic ankle joint 10 between a dorsiflexed position 150 (represented by dash-dot line in FIG. 6), a mid-stance position 152 (represented by short dash-long dash line in FIG. 6), and a plantarflexed position 154 (represented by dash-double dot line in FIG. 6). The prosthetic ankle joint 10 is designed to simulate the movements of an actual human ankle and foot throughout the stance and swing phases of the gate cycle. In the stance phase, the foot is in contact with the ground and the weight of a person is supported on the foot. In the swing phase, the foot is off the ground as the entire leg and foot move from a posterior position to an anterior position with respect to the person's center of gravity. The stance phase begins just after completion of the swing phase and commences with a heel strike wherein the foot is lowered to the ground as the body moves forward from a posterior position. Immediately after heel strike, the foot 12 moves from the dorsiflexed position 150, through the mid-stance position 152 to the plantarflexed position 154, during which time the entire sole of the foot (or shoe) contacts the ground.

Figure 7:
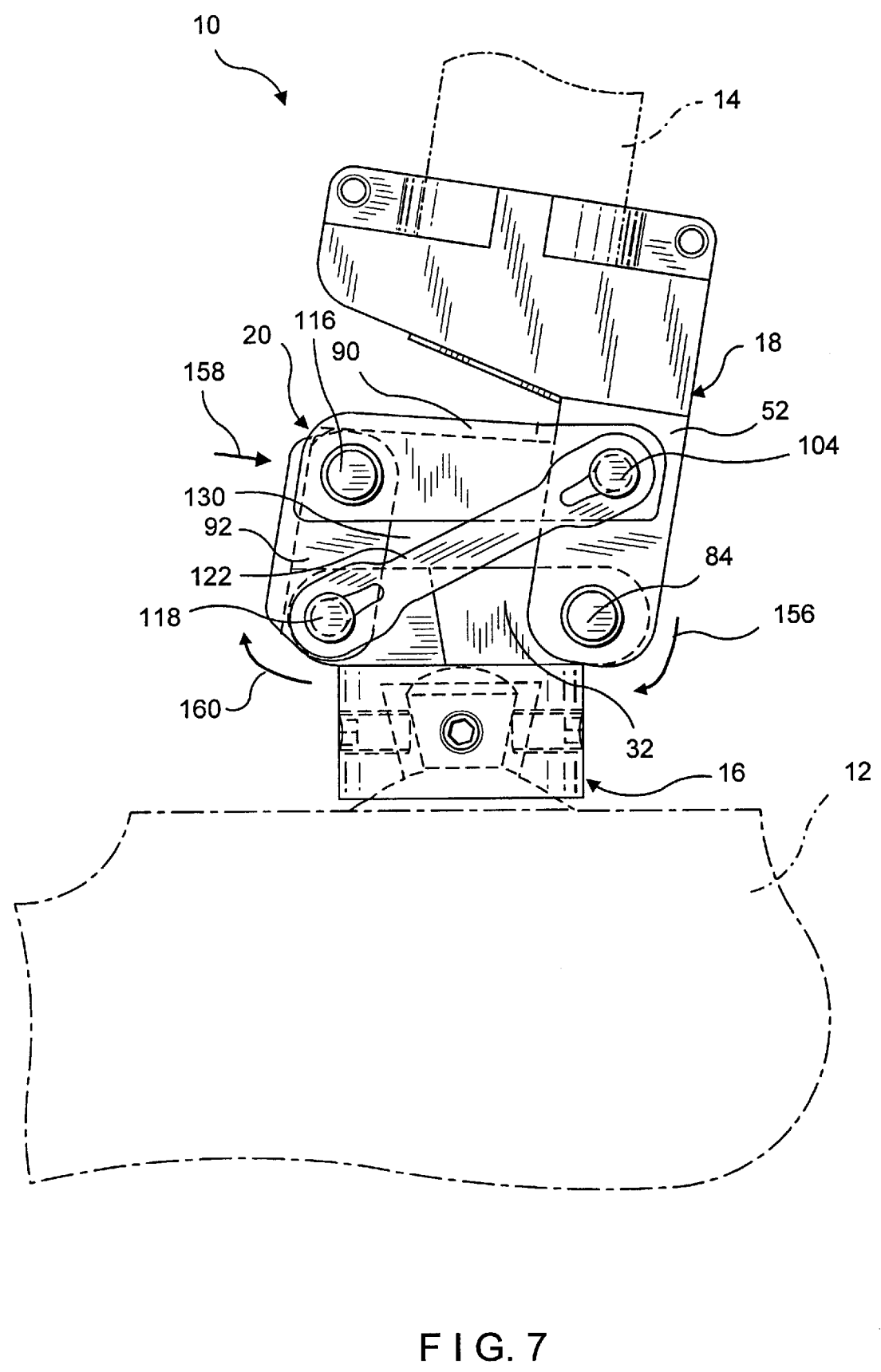

As shown in FIGS. 7 and 12, the weight of the person is used advantageously in the present invention to cause the bottom of the foot 12 to contact the ground. The torque bracket 18, including the posterior upright bar (depending arm) 52 moves in a clockwise direction 156 as viewed in FIG. 7 (counter-clockwise as viewed in FIG. 12) about the lower posterior shaft 84 as the person transfers his or her weight to the foot 12. Rotational movement of the posterior upright bar 52 in this manner causes the upper recumbent bar 90 to translate in a rear direction 158 and the anterior upright bar 92 to rotate in a direction 160 similar to the direction 156. Consequently, the distance between the lower anterior shaft 118 and the upper posterior shaft 104 is increased, while the distance between the upper anterior shaft 116 and the lower posterior shaft 84 is decreased. Simultaneously, the biasing members 120, 122 are stretched and the resilient block 130 is deformed from the initial dorsiflexed position 150 (shown in dash-dot line in FIG. 12) to the plantarflexed position 154 to thereby offer controlled resistance against movement of the four-bar linkage assembly. Preferably, the minimum amount of rotation from vertical to the plantarflexed position is at least 30°. However, the amount of rotation can vary greatly depending on the particular needs of an individual. For example, a person with a relatively long stride will require more plantarflexion than a person with a relatively short stride in order to obtain more surface contact between the foot 12 and the walking surface. The type and hardness of the materials used for the resilient block and biasing members can be chosen to control and adjust the amount of movement, as well as the resistance to movement between the foot 12 and the pylon 14 for a wide variety of people with different weights, heights, stride lengths, walking speeds, and so on.

An important advantage of the above-described arrangement is that contact forces that would normally travel through the leg in prior art devices are now dissipated into the ground. As the heel of the foot 12 contacts the ground, the contact force is transmitted through the ankle and is dissipated through the forward part of the foot 12 and ground as the prosthetic ankle joint 10 moves to the plantarflexed position.

Figure 8:
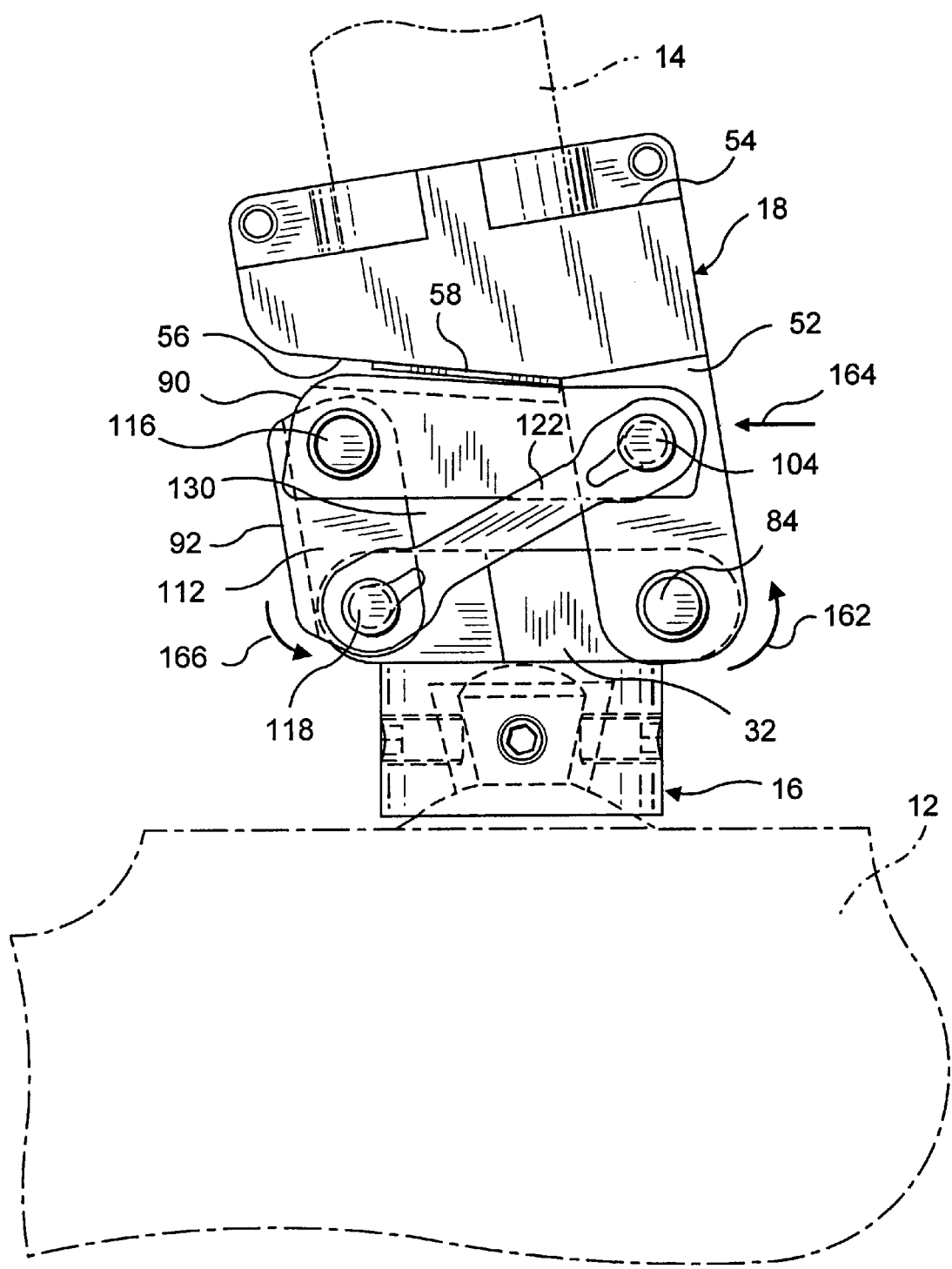
FIG. 8 is a side elevational view of the prosthetic ankle joint in a dorsiflexed position.

As shown in FIGS. 8 and 10, as the prosthetic ankle joint 10 passes from the plantarflexed position, through the midstance position and to the dorsiflexed position, the posterior upright bar (depending arm) 52 is forced in a counter-clockwise rotational direction 162 as viewed in FIG. 8 (clockwise as viewed in FIG. 10) about the lower posterior shaft 84 due to bias forces from the resilient block and biasing members, and the movement of the person's center of gravity forward of the prosthetic ankle joint 10. Rotational movement of the posterior upright bar 52 in this manner causes the upper recumbent bar 90 to translate in a forward direction 164 and the anterior upright bar 92 to rotate in a direction 166 similar to the direction 162. Consequently, the distance between the lower anterior shaft 118 and the upper posterior shaft 104 is decreased, while the distance between the upper anterior shaft 116 and the lower posterior shaft 84 is increased. Simultaneously, the biasing members 120, 122 contract and the resilient block 130 moves to its original shape in the initial dorsiflexed position. As the foot 12 is lifted from the ground to enter the swing phase of the gate cycle, the prosthetic ankle joint 10 will remain in the dorsiflexed position. In this position, and as shown in FIG. 8, the resilient pad 58 on the lower surface 56 preferably abuts the upper bar 90 to thereby provide a measure of cushion between the lower surface and the upper bar.

The amount of dorsiflexion, i.e. the angle between the longitudinal axis of the pylon 14 and the longitudinal extent of the foot 12, is influenced by the angle between the lower surface 56 of the upper leg 50 and the lower leg 52. Preferably, the amount of dorsiflexion is approximately 10 to 12 degrees, which provides one to one and one-half inches of clearance between the walking surface and the foot 12 during the swing phase so that the foot does not catch the walking surface. Of course, more or less clearance can be provided by adjusting the amount of dorsiflexion.

Operation of the prosthetic ankle joint in the above-described manner enables a user to walk with a prosthetic limb of a length equal to a natural limb. Also, greater stability and traction are achieved at heel strike and subsequent plantarflexion motion to thereby provide a greater contact area between the foot (or a shoe placed over the foot) and the walking surface.

Figure 13:
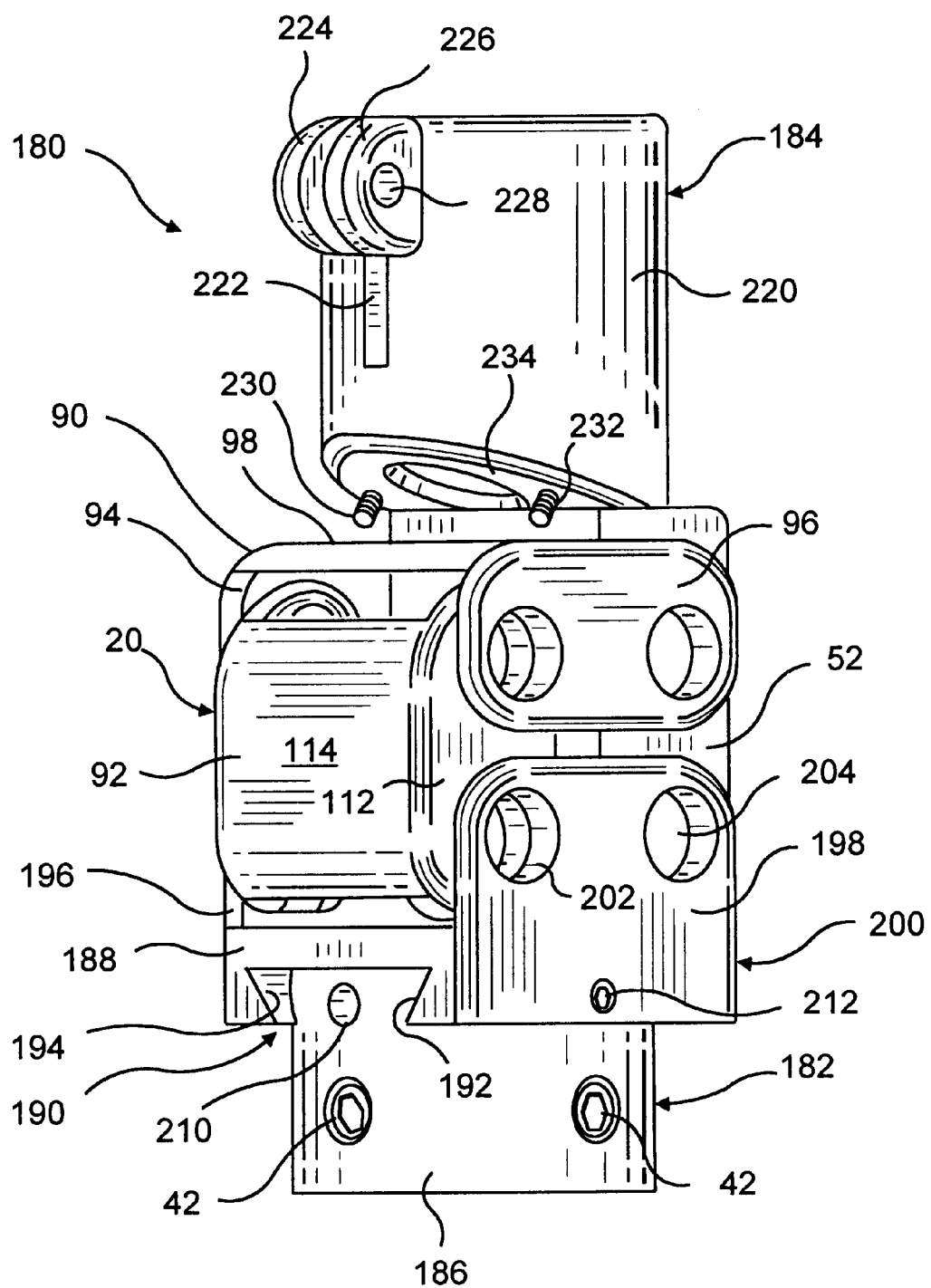
FIG. 13 is a semi-orthogonal view of a prosthetic ankle joint according to a second embodiment of the invention.

With reference now to FIGS. 13 and 14, a prosthetic ankle joint 180 according to a second embodiment of the invention is illustrated, wherein like parts in the previous embodiment are represented by like numerals. The prosthetic ankle joint 180 is similar in construction to the prosthetic ankle joint 10, with the exception of a modified base assembly 182 and a modified torque bracket 184.

The base assembly 182 has a lower base portion 186 and an upper base portion 188 slidably connected to the lower base portion through a dove-tail joint 190. The dove-tail joint 190 includes a generally triangular-shaped projection 192 formed on the lower base portion 186 and a generally trapezoidal-shaped groove 194 formed in the upper base portion 188.

The upper base portion 188 includes a pair of legs 196 and 198 that form a lower recumbent bar 200. Openings 202 and 204 are formed in each leg 196, 198 for receiving the lower anterior shaft 118 (see FIG. 1, for example) and the lower posterior shaft 84, respectively. A tab 206 (see FIG. 14) projects downwardly from a bottom of the slot 194 and into a groove 208 (shown in dashed line) formed in the projection 192 in the lower base portion 186. Preferably, the tab includes a threaded opening (not shown) in alignment with an opening 210 in the lower base portion 186. A threaded shaft or stud (not shown) is captivated in the opening 210 and engages the threaded opening in the tab. Preferably, a set of screws 212 (only one shown) is mounted in each leg 196, 198 and engages the projection 192 for locking the upper and lower base portions against relative sliding movement. Adjustment of the upper base portion 188 with respect to the lower base portion 186 is accomplished by loosening the set screws 212 and then turning the threaded shaft in a desired direction in the lower base portion 186 to thereby cause relative sliding movement between the upper base portion 188 (and thus the four-bar linkage assembly 20), and the lower base portion 186. Movement of the upper base portion with respect to the lower base portion shifts the center of gravity over different parts of the foot 12 to thereby increase the stability of a user during use of the prosthetic ankle joint 180. The stability of a user during walking changes from individual to individual and can depend from such factors as body weight, height, foot size, type of shoe worn, stride length, and so on. By shifting the four-bar linkage unit toward a more anterior or posterior position with respect to the foot 12, it is possible to regulate how quickly the foot reaches a stable plantarflexed position by increasing or decreasing a lever arm defined between the lower posterior shaft 84 and the strike point of the heel on the foot portion 12.

The torque bracket 184 is similar in construction to the torque bracket 18 of the previous embodiment, with the exception that a split collar 220 replaces the upper generally horizontal leg 50 and the mounting bracket 60 of the previous embodiment. The collar 220 is preferably of hollow cylindrical construction and includes a generally vertically extending slot 222 and a pair of tabs 224, 226 located at either side of the slot. Each tab includes an opening 228 that receives a fastener (not shown) in a well-known manner for drawing the slot closed. When a pylon 14 (FIG. 1) is inserted into the collar 220, the slot is drawn closed to thereby tighten the collar around the pylon 14. A pair of adjustment screws 230, 232 are mounted to a lower surface 234 of the collar 220. The adjustment screws project downwardly and forwardly from the lower surface 234 and are adapted to rest on the web 98 of the upper recumbent bar 90 when the linkage assembly 20 is in the plantarflexed position. The adjustment screws 230, 232 can be turned to vary their amount of projection from the lower surface 234. In this manner, it is possible to decrease or increase the angle of the pylon 14 with respect to the foot 12, and thus the amount of dorsiflexion, in order to adjust for a person's walking or gate pattern with respect to the action of the foot.

In addition to, or as an alternative to modifying the resilient block and elastic members in each of the above-described embodiments, the length of the torque bracket, including the depending arm 52 can be increased or decreased in order to change the response rate of the four-bar linkage system under applied load.

A particular advantage with the above-described embodiments over the prior art is the ability to install a foot 12 onto the prosthetic ankle unit that is comfortable to the amputee. Over the years, an amputee learns how to walk with a certain foot and becomes accustomed to the "feel" of that foot. The base assembly 16 of the present invention is readily adaptable to different foot styles and sizes. It is therefore no longer necessary for the amputee to be stuck with a premounted foot as in the prior art arrangements.

It is to be understood that the terms inner, outer, upper, lower, vertical, horizontal, upright, recumbent, anterior, posterior, and their respective derivatives as used throughout the specification refer to relative, rather than absolute positions or orientations.

While the invention has been taught with specific reference to the above-described embodiments, those skilled in the art will recognize that changes can be made in form and detail without departing from the spirit and the scope of the invention. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The embodiments for which an exclusive property or privilege is claimed are defined as follows:

1. A prosthetic ankle joint for connection between a pylon and a prosthetic foot for moving the foot between dorsiflexed and plantarflexed positions, the prosthetic ankle joint comprising:

a base member adapted for connection to the prosthetic foot;

a bracket member adapted for connection to the pylon; and a collapsible and expandable linkage assembly including a first recumbent bar at least operatively associated with the base member, a first upright bar having a lower end pivotally connected to the first recumbent bar at a first pivot joint and an upper end fixedly connected to the bracket member, a second upright bar having a lower end pivotally connected to the first recumbent bar at a second pivot joint, and a second recumbent bar pivotally connected between the first and second upright bars at third and fourth pivot joints, respectively, the first and second upright bars together with the first and second recumbent bars forming an interior space;

wherein pivotal movement between the bracket member and the base member between dorsiflexed and plantarflexed positions causes deformation of the interior space.

2. A prosthetic ankle joint according to claim 1, and further comprising a resilient member positioned in the interior space, the resilient member normally biasing the base member to the dorsiflexed position and resisting rotational movement of the base member from the dorsiflexed position.

3. A prosthetic ankle joint according to claim 2, wherein the resilient member is an elastomeric block.

4. A prosthetic ankle joint according to claim 3, and further comprising at least one biasing member connected between the second pivot joint and the fourth pivot joint to thereby bias the base member in the dorsiflexed position.

5. A prosthetic ankle joint according to claim 3, wherein the elastomeric block is of parallelepiped configuration.

6. A prosthetic ankle joint according to claim 5, and further comprising at least one biasing member connected between the second pivot joint and the fourth pivot joint to thereby bias the base member in the dorsiflexed position.

7. A prosthetic ankle joint according to claim 1, wherein the base member comprises a lower base portion adapted for connection to the prosthetic foot and an upper base portion, and further wherein the first recumbent bar is formed integrally with the upper base portion.

8. A prosthetic ankle joint according to claim 7, wherein the upper base portion is slidably mounted on the lower base portion.

9. A prosthetic ankle joint according to claim 8, and further comprising a dovetail-shaped projection formed on one of the upper and lower base portions and a dovetail-shaped groove formed on the other of the upper and lower base portions, the projection being slidable within the groove to thereby limit sliding movement between the upper base portion and lower base portion in a linear direction.

10. A prosthetic ankle joint according to claim 1, wherein the bracket member is generally L-shaped and includes a generally horizontally extending leg adapted for connection to the pylon and the first upright bar extending generally downwardly from the leg.

11. A prosthetic ankle joint according to claim 10, wherein the leg includes a lower surface that slopes downwardly toward the first upright bar, the lower surface being adapted for engaging the second recumbent bar in the dorsiflexed position to thereby limit the amount of dorsiflexion between the bracket member and the base member.

12. A prosthetic ankle joint according to claim 11, and further comprising a shock absorbing pad on the lower surface for contacting the second recumbent bar in the dorsiflexed position.

13. A prosthetic ankle joint according to claim 11, and further comprising a split collar extending generally upwardly from an upper surface of the leg for receiving and holding the pylon.

14. A prosthetic ankle joint for connection between a pylon and a prosthetic foot for moving the foot between dorsiflexed and plantarflexed positions, the prosthetic ankle joint comprising:

a base member adapted for connection to the prosthetic foot;

a bracket member adapted for connection to the pylon, the bracket member being pivotally connected to the base member at a first pivot joint;

a collapsible and expandable linkage assembly including a recumbent bar pivotally connected to the bracket member at a second pivot joint; and an upright bar having a lower end pivotally connected to the base member at a third pivot joint and an upper end pivotally connected to the recumbent bar at a fourth pivot joint, the bracket member together with the base member, the recumbent bar and the upright bar forming an interior space;

wherein pivotal movement between the bracket member and the base member between dorsiflexed and plantarflexed positions causes deformation of the interior space.

15. A prosthetic ankle joint according to claim 14, and further comprising a resilient member positioned in, and at least substantially filling the interior space, the resilient member normally biasing the base member to the dorsiflexed position and resisting rotational movement of the base member from the dorsiflexed position.

16. A prosthetic ankle joint according to claim 15, wherein the resilient member is an elastomeric block.

17. A prosthetic ankle joint according to claim 16, and further comprising at least one biasing member connected between the second pivot joint and the fourth pivot joint to thereby bias the base member in the dorsiflexed position.

18. A prosthetic ankle joint according to claim 16, wherein the elastomeric block is of parallelepiped configuration.

19. A prosthetic ankle joint according to claim 18, and further comprising at least one biasing member connected between the second pivot joint and the fourth pivot joint to thereby bias the base member in the dorsiflexed position.

* * * * *